(12) United States Patent
Isogawa

(10) Patent No.: US 11,262,428 B2
(45) Date of Patent: Mar. 1, 2022

(54) MAGNETIC RESONANCE IMAGING APPARATUS AND MEDICAL COMPLEX IMAGE PROCESSING APPARATUS

(71) Applicant: Canon Medical Systems Corporation, Otawara (JP)

(72) Inventor: Kenzo Isogawa, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 62 days.

(21) Appl. No.: 16/720,281

(22) Filed: Dec. 19, 2019

(65) Prior Publication Data
US 2020/0209333 A1 Jul. 2, 2020

(30) Foreign Application Priority Data
Dec. 26, 2018 (JP) .............................. JP2018-242501

(51) Int. Cl.
*G06T 5/00* (2006.01)
*G01R 33/56* (2006.01)
(Continued)

(52) U.S. Cl.
CPC .......... *G01R 33/5608* (2013.01); *A61B 5/055* (2013.01); *G01R 33/543* (2013.01);
(Continued)

(58) Field of Classification Search
CPC .. G06T 5/50; G06T 5/003; G06T 5/20; G06T 5/10; G06T 5/001; G06T 5/30;
(Continued)

(56) References Cited

U.S. PATENT DOCUMENTS

2002/0094114 A1   7/2002 Ogino
2009/0102481 A1*  4/2009 Haacke ............... G01R 33/565
                                                        324/318
(Continued)

FOREIGN PATENT DOCUMENTS

EP   2708909 A2 *  3/2014  ....... G01R 33/56545
JP   06-022928 A   2/1994
(Continued)

OTHER PUBLICATIONS

Extended European Search Report dated Apr. 1, 2020 in Patent Application No. 19217168.4, 15 pages.
(Continued)

*Primary Examiner* — Jose L Couso
(74) *Attorney, Agent, or Firm* — Oblon, McClelland, Maier & Neustadt, L.L.P.

(57) ABSTRACT

According to one embodiment, a magnetic resonance imaging apparatus includes processing circuitry. The processing circuitry is configured to apply a filter to each of a first real-part image and a first imaginary-part image of a first complex image generated based on acquired magnetic resonance data and thereby generate a second complex image that includes a second real-part image and a second imaginary-part image. The processing circuitry is configured to generate a phase image denoised by the filter, the denoised phase image generated based on the second real-part image and the second imaginary-part image. The processing circuitry is configured to generate an intensity image related to an absolute value of the first complex image based on pixel values of the denoised phase image, the first real-part image, and the first imaginary-part image.

10 Claims, 9 Drawing Sheets

(51) Int. Cl.
*A61B 5/055* (2006.01)
*G01R 33/54* (2006.01)
*G06T 5/50* (2006.01)

(52) U.S. Cl.
CPC .............. *G06T 5/002* (2013.01); *G06T 5/50* (2013.01); *G06T 2207/10088* (2013.01)

(58) Field of Classification Search
CPC . G06T 2207/10088; G06T 2207/20081; G06T 2207/20084; G06T 2207/20064; G06T 2207/20192; G06T 2207/10096; G06T 2207/30004; G06T 2207/20032; G06T 2207/20221; G06T 11/006; G06T 7/0012; G01R 33/5608; G01R 33/543; G01R 33/4828; G01R 33/4836; G01R 33/546; G01R 33/5602; G01R 33/5613; G01R 33/5635; G01R 33/56509; G01R 33/56536; G01R 33/243; G01R 33/4835; G01R 33/5601; G01R 33/5611; G01R 33/563; G01R 33/56545; G01R 33/56341; G01R 33/565; G01R 33/4816; G01R 33/4824; G01R 33/4818; G01R 33/24; G01R 33/28; G01R 33/32; G01R 33/38; G01R 33/54; G01R 33/56; G01R 33/56563; A61B 5/055; A61B 5/0042; A61B 5/7203; A61B 5/7225; A61B 5/7253; A61B 6/032; A61B 6/5206; A61B 6/5258; A61B 8/5207; A61B 8/5269; G06K 9/40; G06K 9/00516; G06K 9/4628; G06K 2209/05; G06N 20/00; G06N 20/10; G06N 3/0472; G06N 3/08; G06N 7/005; G16H 30/40; G16H 50/70; G16H 50/20; G01N 23/041
See application file for complete search history.

(56) References Cited

U.S. PATENT DOCUMENTS

| | | | | |
|---|---|---|---|---|
| 2010/0239151 A1* | 9/2010 | Dannels | ............... | G01R 33/246 382/131 |
| 2011/0304330 A1* | 12/2011 | Yoneda | ............... | A61B 5/0042 324/309 |
| 2012/0074940 A1* | 3/2012 | Kimura | ............. | G01R 33/4818 324/314 |
| 2013/0293231 A1 | 11/2013 | Hirai | | |
| 2014/0066767 A1* | 3/2014 | Mammone | ........... | A61B 8/5269 600/442 |
| 2014/0153692 A1* | 6/2014 | Larkin | ...................... | G06T 5/10 378/36 |
| 2014/0233825 A1* | 8/2014 | Yoneda | .................. | G01R 33/56 382/131 |
| 2015/0310641 A1* | 10/2015 | Purdy | .................. | G01R 33/565 382/131 |
| 2017/0059682 A1* | 3/2017 | Dagher | ................ | G01R 33/243 |
| 2018/0089863 A1* | 3/2018 | Marschner | ......... | G01R 33/5608 |
| 2019/0130564 A1* | 5/2019 | Kawabata | ........... | G06K 9/2054 |
| 2019/0137589 A1 | 5/2019 | Noguchi et al. | | |
| 2020/0191892 A1* | 6/2020 | Corum | .............. | G01R 33/3642 |
| 2020/0393526 A1* | 12/2020 | Wang | ................. | G01R 33/5615 |

FOREIGN PATENT DOCUMENTS

| | | |
|---|---|---|
| JP | 4149126 B2 | 9/2008 |
| JP | 2017-209329 A | 11/2017 |
| WO | WO 2012/098955 A1 | 7/2012 |

OTHER PUBLICATIONS

P. Borrelli, et al., "Improving SNR in Susceptibility Weighted Imaging by a NLM-Based Denoising Scheme" 2014 IEEE International Conference on Imaging Systems and Techniques (1st) Proceedings, IEEE, XP032685457, Oct. 14, 2014, pp. 346-350.

Douglas C. Noll, et al., "Homodyne Detection in Magnetic Resonance Imaging" IEEE Transactions on Medical Imaging, IEEE Service, Center, Piscataway, NJ, US, vol. 10, No. 2, XP000234750, Jun. 1, 1991, pp. 154-163.

Cornelius Eichner, et al., "Real Diffusion-Weighted MRI Enabling True Signal Averaging and Increased Diffusion Contrast" NeuroImage, vol. 122, XP055655788, Aug. 1, 2015, pp. 373-384.

Douglas E. Prah, et al., "A Simple Method for Rectified Noise Floor Suppression: Phase-Corrected Real Data Reconstruction with Application to Diffusion-Weighted Imaging" Magnetic Resonance in Medicine, vol. 64, No. 2, XP055104082, May 25, 2010, pp. 418-429.

* cited by examiner

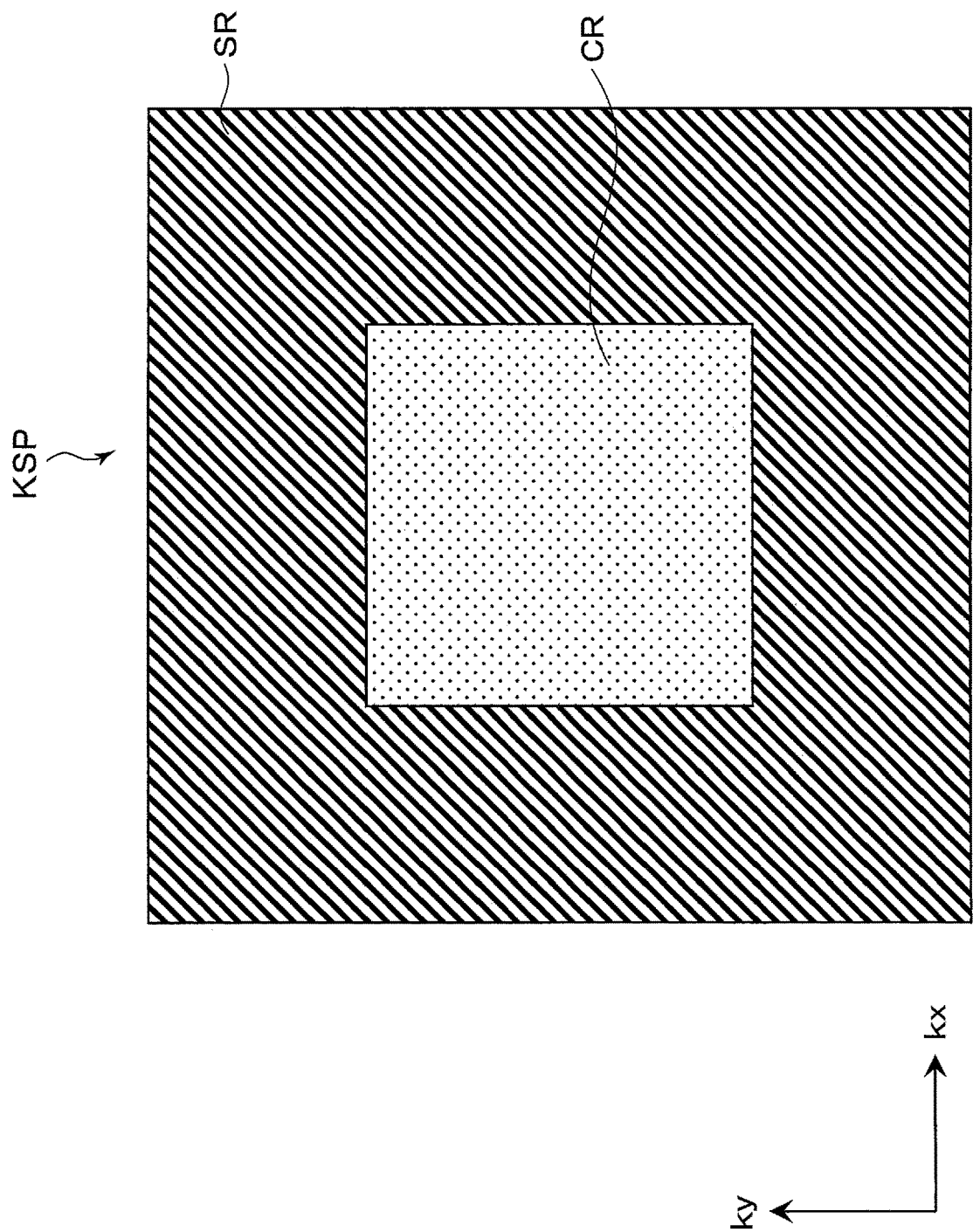
F I G. 4

MAGNETIC RESONANCE IMAGING APPARATUS AND MEDICAL COMPLEX IMAGE PROCESSING APPARATUS

CROSS-REFERENCE TO RELATED APPLICATIONS

This application is based upon and claims the benefit of priority from the prior Japanese Patent Application No. 2018-242501, filed Dec. 26, 2018, the entire contents of which are incorporated herein by reference.

FIELD

Embodiments described herein relate generally to a magnetic resonance imaging apparatus and a medical complex image processing apparatus.

BACKGROUND

A magnetic resonance imaging (hereinafter referred to as "MRI") apparatus generates a grayscale image (also referred to as an "intensity image" or an "absolute-value image") from a complex image by performing non-linear transformation (also referred to as "polar coordinate transformation") $\{(\text{ReI})^2+(\text{ImI})^2\}^{1/2}$ on a real-part image ReI and an imaginary-part image ImI of the complex image. At this time, the nature of noise changes due to the polar coordinate transformation from the complex image to the grayscale image, that is, the sum of squares and square root. Namely, a Gaussian noise, which is an additive noise that follows a Gaussian distribution in the complex image, is transformed, through the polar coordinate transformation, into a noise that follows a Rayleigh distribution in the grayscale image. A difference between a Gaussian distribution and a Rayleigh distribution is that an average of a probability density distribution function of the Gaussian distribution is zero, whereas an average of a probability density distribution function of the Rayleigh distribution is not zero, that is, the probability density distribution function representing the Rayleigh distribution does not have negative values. Thus, a bias of noise whose average is not zero is superimposed on the grayscale image. Accordingly, the grayscale image resembles a haze with unnaturally whitish parts (hereinafter referred to as "black floating").

The black floating is caused by the non-linear transformation used when generating a grayscale image from a complex image, as described above. Namely, since a pixel value that should originally be a negative value is distorted to be a positive value through the non-linear transformation because of noise, black floating proportional to the noise amount occurs. Therefore, even if a smoothing filter is applied to the grayscale image in order to denoise the grayscale image, the issue of black floating cannot be resolved because the bias having the Rayleigh distribution in which a noise average is positive is superimposed on the grayscale image.

To suppress black floating, the measures described below can be taken. First, the noise amount of the grayscale image is estimated from a mode value of a histogram of a variance (or standard deviation) of pixel values in a local region that includes a pixel of interest in the grayscale image generated from the complex image through the non-linear transformation. Next, if the variance in each local region of the grayscale image is smaller than a threshold determined based on the noise amount, the pixel value of the pixel of interest corresponding to the local region is multiplied by a coefficient smaller than 1, to suppress the black floating in the grayscale image.

The measures described above compensate for the black floating by estimating the noise amount from a standard deviation of a portion of the grayscale area where a variation of the pixel value is flat (i.e., flat portion). When the noise amount is estimated in the complex image using a standard deviation of a texture in the edge and the body tissue in order to discriminate between the texture and the noise, a region of sufficient breadth is needed in order to improve the accuracy of noise amount estimation. However, if a region of the flat portion of the pixel value of the complex image is small, the accuracy of the noise amount estimation may degrade. Therefore, if the noise amount is overestimated in the grayscale image, a pixel value of a bright portion of the grayscale image decreases, and if the noise amount is underestimated in the grayscale image, the black floating may not disappear.

BRIEF DESCRIPTION OF THE DRAWINGS

FIG. 4 is a diagram showing an example of a k-space having zero padding according to the present embodiment.

DETAILED DESCRIPTION

According to one embodiment, a magnetic resonance imaging apparatus includes processing circuitry. The processing circuitry is configured to apply a filter to each of a first real-part image and a first imaginary-part image of a first complex image generated based on acquired magnetic resonance data and thereby generate a second complex image that includes a second real-part image and a second imaginary-part image. The processing circuitry is configured to generate a phase image denoised by the filter, the denoised phase image generated based on the second real-part image and the second imaginary-part image. The processing circuitry is configured to generate an intensity image related to an absolute value of the first complex image based on pixel values of the denoised phase image, the first real-part image, and the first imaginary-part image.

The purpose is to generate a medical image with noise reduced.

Hereinafter, embodiments of a magnetic resonance imaging apparatus (hereinafter referred to as an "MRI apparatus") will be described with reference to the drawings. In the description below, structural elements having substantially the same functions and configurations will be denoted by the same reference symbols, and a repetitive description of such elements will be given only where necessary.

In the description below, an intensity image related to an absolute value of a complex image (said intensity image generated based on a denoised phase image, a real-part image, and an imaginary-part image) may be referred to as a "pseudo intensity image", to clarify the difference with a grayscale image (intensity image) generated from a complex image through non-linear transformation performed on a real-part image and an imaginary-part image of the complex image.

Embodiments

Figure 1:
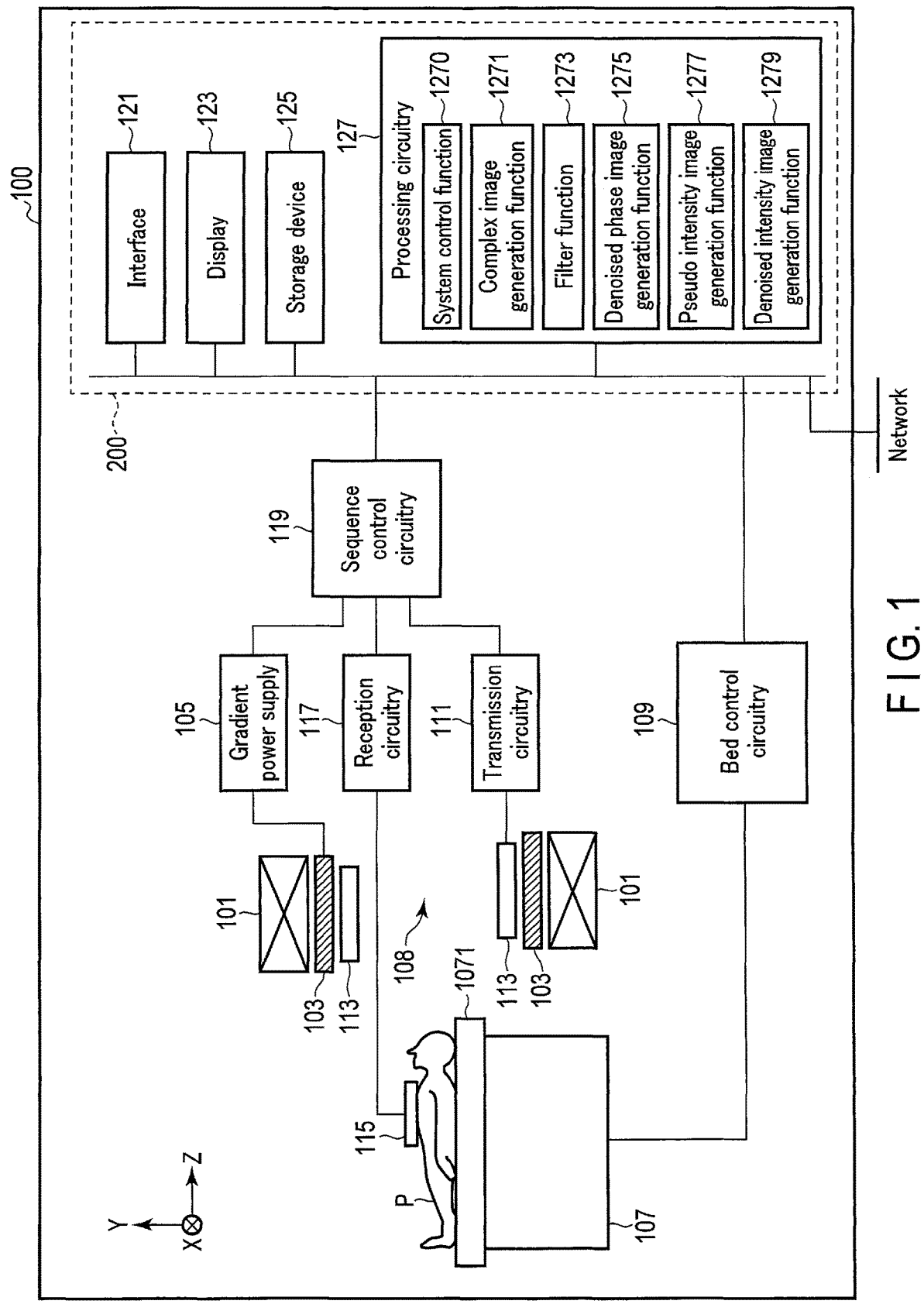
FIG. 1 is a diagram showing an example of a configuration of a magnetic resonance imaging apparatus according to the present embodiment.

An overall configuration of an MRI apparatus 100 of the present embodiment will be described with reference to FIG. 1. FIG. 1 shows a configuration of the MRI apparatus 100 of the present embodiment. As shown in FIG. 1, the MRI apparatus 100 includes a static field magnet 101, a gradient coil 103, a gradient power supply 105, a bed 107, bed control circuitry 109, transmission circuitry (transmitter) 111, a transmitter coil 113, a receiver coil 115, reception circuitry (receiver) 117, sequence control circuitry (sequence controller) 119, an interface (input unit) 121, a display 123, a storage device (storage unit, memory) 125, and processing circuitry (processor) 127. The MRI apparatus 100 may include a hollow cylindrical shim coil between the static field magnet 101 and the gradient coil 103.

The static field magnet 101 is a hollow, approximately-cylindrical magnet. The static field magnet 101 is not necessarily approximately cylindrical, and may be formed in an open shape. The static field magnet 101 generates a uniform static magnetic field in its inner space. For example, a superconductive magnet or the like is used as the static field magnet 101.

The gradient coil 103 is a hollow cylindrical coil. The gradient coil 103 is provided on the inner side of the static field magnet 101. The gradient coil 103 is formed by combining three coils respectively corresponding to the X-, Y-, and Z-axes that are orthogonal to one another. The Z-axis direction is the same as the direction of the static magnetic field. The Y-axis direction is a vertical direction, and the X-axis direction is a direction perpendicular to the Z-axis and the Y-axis. The three coils of the gradient coil 103 individually receive a current supplied from the gradient power supply 105, and generate gradient fields in which the magnetic field intensity changes along each of the X-, Y-, and Z-axes.

The gradient fields in the X-, Y-, and Z-axes generated by the gradient coil 103 respectively correspond to, for example, a slice selection gradient field, a phase encode gradient field, and a frequency encode gradient field (also referred to as a "readout gradient field"). The slice selection gradient field is used to determine an imaging slice as appropriate. The phase encode gradient field is used to change a phase of a magnetic resonance (hereinafter referred to as "MR") signal in accordance with a spatial position. The frequency encode gradient field is used to change a frequency of an MR, signal in accordance with a spatial position.

The gradient power supply 105 is a power supply apparatus that supplies a current to the gradient coil 103 under the control of the sequence control circuitry 119.

The bed 107 is an apparatus with a top plate 1071 on which a subject P is placed. The bed 107 inserts the top plate 1071, on which the subject P is placed, into a bore 108 under the control of the bed control circuitry 109. The bed 107 is installed in an examination room where the present MRI apparatus 100 is installed in such a manner that the longitudinal direction of the bed 107 is parallel to the central axis of the static field magnet 101.

The bed control circuitry 109 is a piece of circuitry that controls the bed 107. The bed control circuitry 109 drives the bed 107 in accordance with an operator's instruction via the interface 121, to thereby move the top plate 1071 in the longitudinal direction and the vertical direction, and, in some cases, in the horizontal direction. The bed control circuitry 109 is mounted in, for example, the bed 107 or a console apparatus equipped with the interface 121, the display 123, the storage device 125, and the processing circuitry 127.

The transmission circuitry 111 is, for example, mounted in a gantry equipped with the static field magnet 101, the gradient coil 103, and the transmitter coil 113. The transmission circuitry 111 is not necessarily mounted in a gantry, and may be mounted in a console apparatus, the bed 107, or the like. Under the control of the sequence control circuitry 119, the transmission circuitry 111 supplies a high-frequency pulse (radio frequency (RF) pulse) modulated to a magnetic resonance frequency (also referred to as "Larmor frequency") to the transmitter coil 113. The magnetic resonance frequency is set in advance according to a gyromagnetic ratio based on an atom of a magnetic resonance object and a magnetic flux density of a static magnetic field. When a magnetic flux density of a static magnetic field is 1.5 T, the magnetic resonance frequency is approximately 64 MHz. When a magnetic flux density of a static magnetic field is 3 T, the magnetic resonance frequency is approximately 128 MHz.

The transmitter coil 113 is an RF coil arranged on the inner side of the gradient coil 103. The transmitter coil 113 receives an RF pulse supplied from the transmission circuitry ill and generates a high-frequency magnetic field. The transmitter coil 113 irradiates the subject P placed in the static magnetic field with the high-frequency magnetic field. The transmitter coil 113 is, for example, a whole-body coil (WB coil) including a plurality of coil elements. The WB coil 113 may be used as a transmitter-receiver coil. The transmitter coil 113 may also be a WB coil 113 made of a single coil. Hereinafter, the transmitter coil 113 will be described as a WB coil 113 capable of transmitting and receiving.

The receiver coil 115 is an RF coil provided on the inner side of the gradient coil 103 in the bore 108. The receiver coil 115 receives an MR signal emitted from the subject P by the imaging (MR imaging) in which the subject. P is irradiated with a high-frequency magnetic field. The receiver coil 115 outputs the received MR signal to the reception circuitry 117. The receiver coil 115 may be formed of a coil array that includes, for example, one or more, typically, a plurality of coil elements (hereinafter referred to as "receiver coil elements").

FIG. 1 shows the WB coil 113 and the receiver coil 115 as separate coils; however, the receiver coil 115 may be implemented as a transmitter-receiver coil that has the function of transmitting the high-frequency magnetic field of the WB coil 113. The transmitter-receiver coil is furnished for the top plate 1071 according to an imaging target of the subject P. The transmitter-receiver coil is a local transmitter-receiver RF coil such as a head coil apparatus.

The reception circuitry 117 generates a digital MR signal (hereinafter referred to as "MR data") based on the MR signal output from the receiver coil 115 under the control of the sequence control circuitry 119. The MR data corresponds to a digital MR signal represented by a complex number. Specifically, the reception circuitry 117 amplifies the MR signal output from the receiver coil 115 via a receiver amplifier (not shown). The reception circuitry 117 performs various types of signal processing on the amplified MR signal, and then performs analog-to-digital (A/D) conversion of data subjected to the various types of signal processing. The reception circuitry 117 thereby generates the MR data. The reception circuitry 117 outputs the generated MR data to the sequence control circuitry 119.

The sequence control circuitry 119 controls the gradient power supply 105, the transmission circuitry 111, the reception circuitry 117, and the like in accordance with a sequence output from the processing circuitry 127, and performs imaging on the subject P. In the sequence, the magnitude of the current supplied to the gradient coil 103 by the gradient power supply 105, the timing at which the current is supplied to the gradient coil 103 by the gradient power supply 105, the magnitude and duration of the RF pulse supplied to the WB coil 113 by the transmission circuitry 111, the timing at which the RF pulse is supplied to the WB coil 113 by the transmission circuitry 111, the timing at which the MR signal is received by the receiver coil 115, and the like are defined according to the inspection type, the sequence type, and the like.

The interface 121 includes circuitry for receiving various instructions and information input from the operator. The interface 121 includes circuitry relating to, for example, a pointing device such as a mouse, or an input device such as a keyboard. The circuitry included in the interface 121 is not limited to circuitry relating to a physical operational component, such as a mouse or a keyboard. For example, the interface 121 may include electric signal processing circuitry that receives an electric signal corresponding to an input operation from an external input device provided separately from the present MRI apparatus 100 and outputs the received electric signal to various types of circuitry. Under the control of the processing circuitry 127, the interface 121 may acquire various data from an external storage device, various modalities, a radiology information management system, or the like, which is coupled to the interface 121 directly or via a network or the like.

Under the control of a system control function 1270 of the processing circuitry 127, the display 123 displays, for example, a denoised intensity image generated by a denoised intensity image generation function 1279 and various types of information regarding imaging and image processing. The display 123 corresponds to, for example, a display device, such as a cathode-ray tube (CRT) display, a liquid crystal display, an organic electroluminescence (EL) display, a light-emitting diode (LED) display, a plasma display, or any other display or monitor known in the relevant technical field.

The storage device 125 stores, for example, MR data filled in the k-space, data of a complex image generated by a complex image generation function 1271, and data of a denoised intensity image as an MR image. The storage device 125 stores, for example, various types of imaging sequences, and imaging conditions including a plurality of imaging parameters that define imaging sequences. The storage device 125 stores programs related to various reconstruction methods used by the complex image generation function 1271.

The storage device 125 stores programs corresponding to various functions executed by the processing circuitry 127. The storage device 125 is, for example, a semiconductor memory element, such as a random access memory (RAM) and a flash memory, a hard disk drive, a solid state drive, or an optical disk. The storage device 125 may be, for example, a drive configured to read and write various kinds of information with respect to a portable storage medium such as a CD-ROM drive, a DVD drive, or a flash memory.

The processing circuitry 127 includes, as hardware resources, a processor, a memory such as a read-only memory (ROM) or a RAM, and the like (not shown), and comprehensively controls the present MRI apparatus 100. The processing circuitry 127 includes the system control function 1270, the complex image generation function 1271, a filter function 1273, a denoised phase image generation function 1275, a pseudo intensity image generation function 1277, and the denoised intensity image generation function 1279. The functions performed by the system control function 1270, the complex image generation function 1271, the filter function 1273, the denoised phase image generation function 1275, the pseudo intensity image generation function 1277, and the denoised intensity image generation function 1279 are stored in the storage device 125 in the form of programs that are executable by a computer. The processing circuitry 127 is a processor that reads the programs corresponding to these functions from the storage device 125 and executes these programs, to thereby implement the functions corresponding to respective programs. In other words, the processing circuitry 127, after having read the respective programs, includes a plurality of functions, etc., presented in the processing circuitry 127 in FIG. 1.

FIG. 1 illustrates that the various functions are implemented by the single processing circuitry 127; however, a plurality of independent processors may be combined to constitute the processing circuitry 127, so that the functions are implemented by the respective processors executing the programs. In other words, each of the above-described functions may be configured as a program so that single processing circuitry executes each program, or a specific function may be implemented in dedicated, independent program-execution circuitry. The system control function 1270, the complex image generation function 1271, the filter function 1273, the denoised phase image generation function 1275, the pseudo intensity image generation function 1277, and the denoised intensity image generation function 1279 included in the processing circuitry 127 are examples of a system controller, a complex image generator, a filter unit, a denoised phase image generation unit, a pseudo intensity image generation unit, and a denoised intensity image generation unit, respectively.

The term "processor" used in the above description means, for example, circuitry such as a central processing unit (CPU), a graphics processing unit (GPU), an application specific integrated circuit (ASIC), or a programmable logic device (e.g., a simple programmable logic device (SPLD), a complex programmable logic device (CPLD), and a field programmable gate array (FPGA)).

The processor implements various functions by reading and executing the programs stored in the storage device 125. The programs may be directly integrated into the circuitry of the processor, instead of being stored in the storage device 125. In this case, the processor implements the functions by reading and executing the programs integrated into the circuitry. Likewise, each of the bed control circuitry 109, the transmission circuitry 111, the reception circuitry 117, the sequence control circuitry 119, and the like may be configured by electronic circuitry, such as the above-described processor.

The processing circuitry 127 comprehensively controls the MRI apparatus 100 through the system control function 1270. Specifically, the processing circuitry 127 reads a system control program stored in the storage device 125, develops the system control program on a memory, and controls the various types of circuitry, etc., of the present MRI apparatus 100 in accordance with the developed system control program. For example, through the system control function 1270, the processing circuitry 127 reads an imaging sequence from the storage device 125 based on imaging conditions input by an operator through the interface 121. The processing circuitry 127 may generate an imaging sequence based on the imaging conditions. The processing circuitry 127 transmits the imaging sequence to the sequence control circuitry 119 and controls imaging of the subject P.

Through the complex image generation function 1271, the processing circuitry 127 generates a first complex image based on MR data collected for the subject P. Specifically, the processing circuitry 127 fills MR data in the readout direction of the k-space in accordance with the intensity of the readout gradient magnetic field. The processing circuitry 127 generates a first complex image by performing a Fourier transform (complex Fourier transform) on the MR data filled in the k-space. The first complex image includes a first real-part image and a second imaginary-part image. The processing circuitry 127 causes the storage device 125 to store the first complex image.

The processing related to the filter function 1273, the denoised phase image generation function 1275, the pseudo intensity image generation function 1277, and the denoised intensity image generation function 1279 executed by the processing circuitry 127 will be described during the description of the process of reducing black floating (hereinafter referred to as a "black-floating reduction process"). "Black floating" refers to a state in which it looks like a unnaturally whitish part is floating in an entire region of an absolute-value image generated based on MR data. The overall configuration of the MRI apparatus 100 according to the present embodiment has been described above. Hereinafter, the black-floating reduction process will be described.

Figure 2:
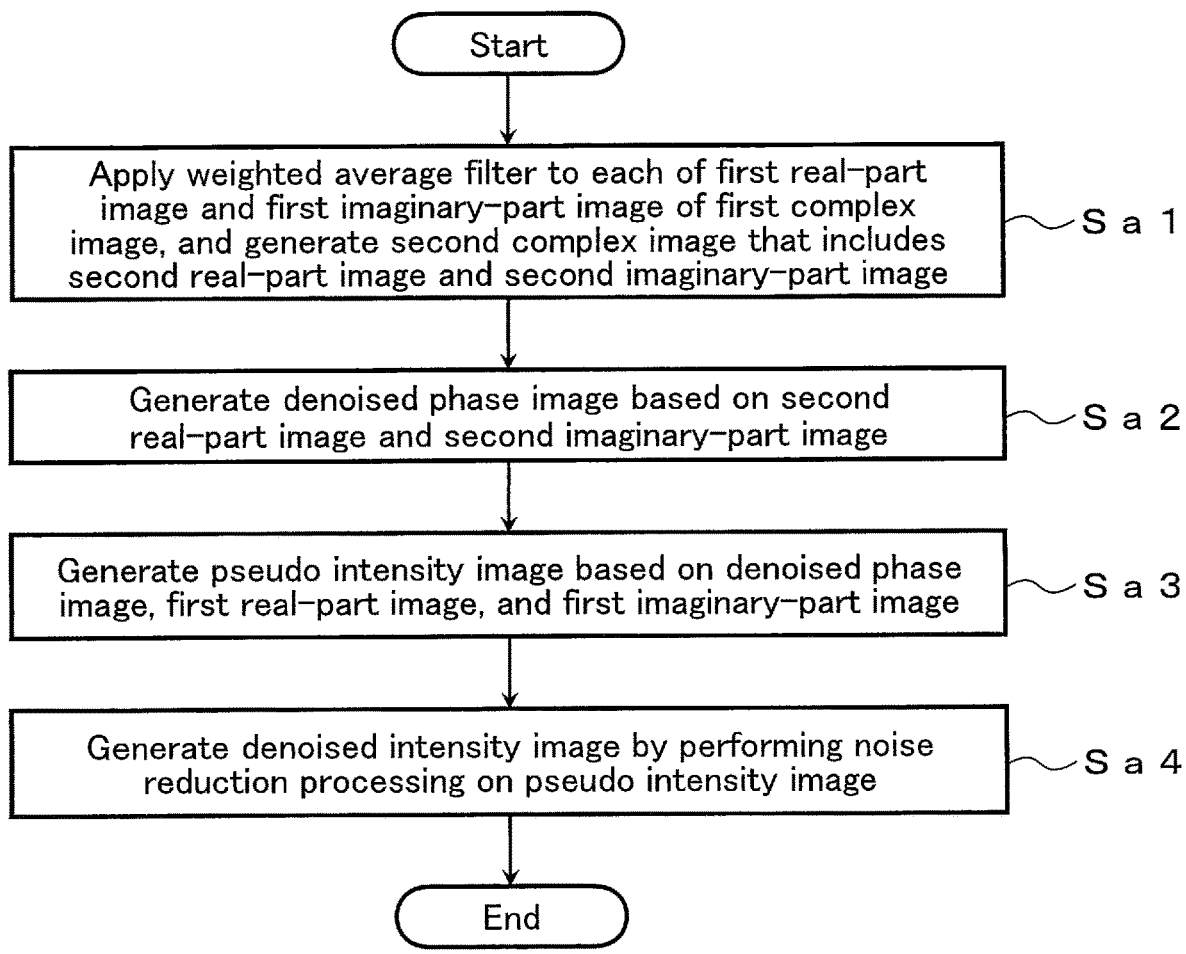
FIG. 2 is a flowchart showing an example of a process of reducing black floating according to the present embodiment.
Figure 3:
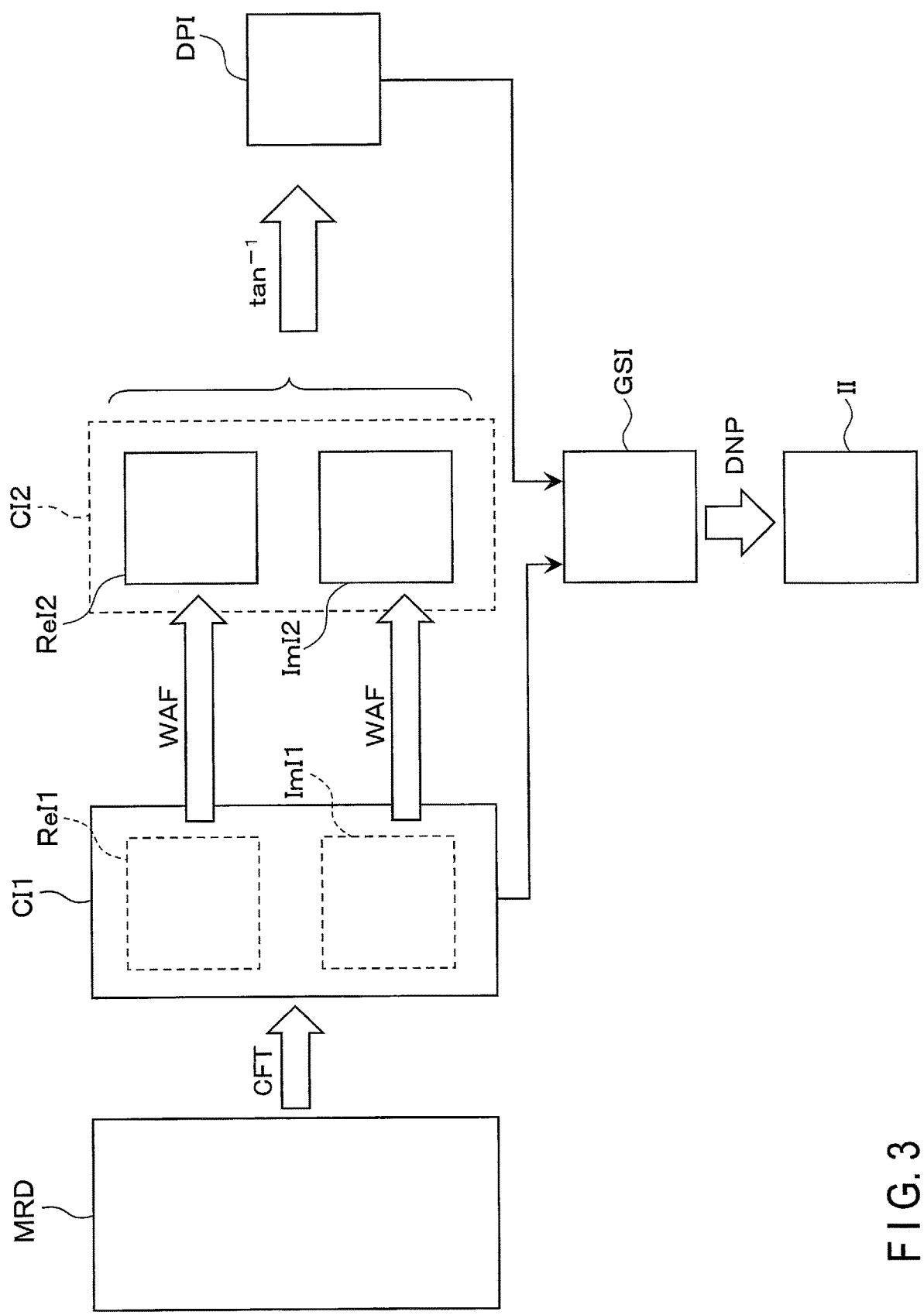
FIG. 3 is a schematic diagram showing an example of a process of generating a pseudo intensity image related to the process of reducing black floating according to the present embodiment.

FIG. 2 is a flowchart showing an example of the black-floating reduction process. FIG. 3 is a schematic diagram showing an example of a process of generating a denoised intensity image related to the black-floating reduction process.

(Black-Floating Reduction Process)

Before performing the black-floating reduction process, the processing circuitry 127, by using the complex image generation function 1271, performs a complex Fourier transform CFT on MR data MRD represented by a complex number, to thereby reconstruct a first complex image CI1. Namely, through said reconstruction, the processing circuitry 127 generates the first complex image CI1 formed of a first real-part image ReI1 and a first imaginary-part image ImI1 based on the MR data MRD. The first complex image CI1 may be generated in advance and stored in the storage device 125. At this time, the processing circuitry 127, by using the filter function 1273, reads the first complex image CI1 from the storage device 125 before performing the black-floating reduction process.

(Step Sa1)

Through the filter function 1273, the processing circuitry 127 applies a weighted average filter WAF to each of the first real-part image ReI1 and the first imaginary-part image ImI1 of the first complex image CI1 independently, to thereby generate a second complex image CI2 that includes a second real-part image ReI2 and a second imaginary-part image ImI2. The weighted average filter WAF is a linear filter having denoising effects and obtained by simple calculation. For example, the weighted average filter WAF may be a low pass filter (hereinafter referred to as "LPF") or a Gaussian filter. Other than the weighted average filter, a filter equivalent to an LPF or Gaussian filter may be adopted.

Specifically, the processing circuitry 127 applies the weighted average filter WAF to the first real-part image ReI1, to thereby generate the second real-part image ReI2. The processing circuitry 127 applies the weighted average filter WAF to the first imaginary-part image ImI1, to thereby generate the second imaginary-part image ImI2. Through the above processing, the processing circuitry 127 generates the second complex image CI2 that includes the second real-part image ReI2 and the second imaginary-part image ImI2.

When a pixel value of a position (x,y) in the first real-part image ReI1 is defined as a(x,y), and a pixel value of a position (x,y) in the first imaginary-part image ImI1 is defined as b(x,y), a pixel value $CI1(x,y)$ of a position (x,y) in the first complex image CI1 is represented by the following formula (1) using an imaginary number j.

$$CI1(x,y)=a(x,y)+j\times b(x,y) \tag{1}$$

When a (kernel) size of the weighted average filter WAF is defined as m×n (m, n being a natural number), and a weight of the weighted average filter WAF is defined as $w_{mn}$, the processing circuitry 127 performs, through the filter function 1273, calculation of the following formula (2), which applies the weighted average filter WAF to the first real-part image ReI1, to thereby generate a pixel value $a_{lpf}(x,y)$ of a position (x,y) in the second real-part image ReI2.

$$a_{lpf}(x, y) = \sum_{m,n} w_{mn} a(m, n) \tag{2}$$

In addition, through the filter function 1273, the processing circuitry 127 performs calculation of the following formula (3), which applies the weighted average filter WAF to the first imaginary-part image ImI1, to thereby generate a pixel value $b_{lpf}(x,y)$ of a position (x,y) in the second imaginary-part image ImI2.

$$b_{lpf}(x, y) = \sum_{m,n} w_{mn} b(m, n) \tag{3}$$

With the formulae (2) and (3), a pixel value $CI2_{lpf}(x,y)$ of the second complex image CI2 is represented by the following formula (4) using an imaginary number j.

$$CI2_{lpf}(x,y) = a_{lpf}(x,y) + j \times b_{lpf}(x,y) \quad (4)$$

Through the filter function 1273, the processing circuitry 127 may suitably adjust the size of the weighted average filter WAF (also referred to as a "kernel size of LPF" or a "tap width of LPF") in accordance with a region related to zero padding and a region where MR data is arranged in the k-space related to the first complex image CI1. For example, if MR data is arranged in a central region in the k-space related to the first complex image CI1 (the central region including a center of the k-space) by assembling the MR data in the central region of the k-space, and zero is arranged in a surrounding region in the k-space excluding the central region, the processing circuitry 127 determines the size of the weighted average filter WAF in accordance with an area ratio of the k-space to the central region. Namely, the processing circuitry 127 determines the size of the weighted average filter WAF in accordance with a proportion of the region of zero padding to the k-space related to the first complex image CI1. Hereinafter, determination (adjustment) of the size of the weighted average filter WAF will be described in detail with reference to FIGS. 4 and 5.

FIG. 4 shows an example of the k-space having zero padding. As shown in FIG. 4, MR data is arranged in a central region CR. Also, zero is arranged in a surrounding region SR. Hereinafter, the central region CR and a k-space KSP related to the first complex image CI1 will be illustrated in square-shaped fashion, to provide concrete descriptions.

Figure 5:
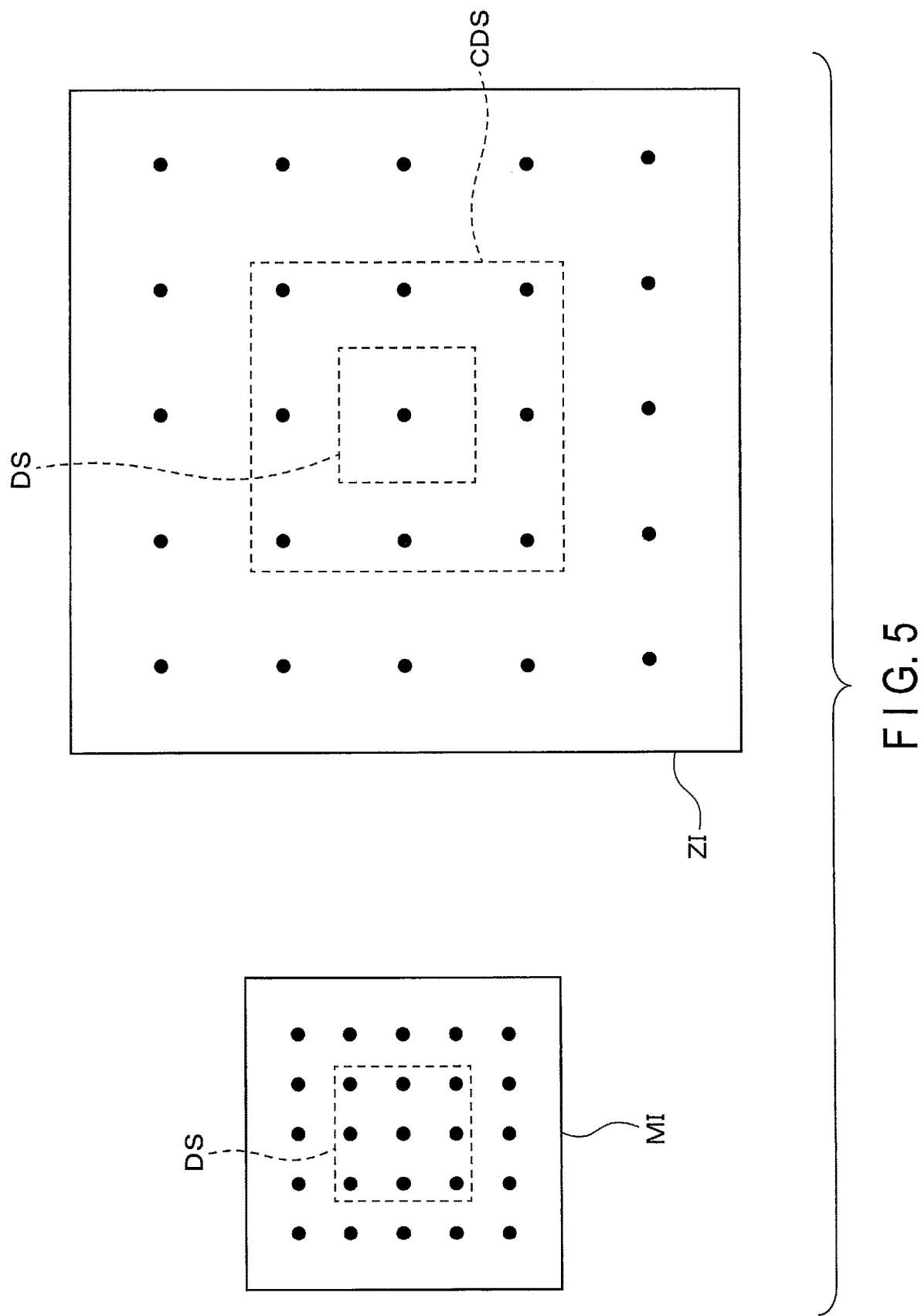
FIG. 5 is a diagram showing an example of an image obtained after performing a Fourier transform on a central region of the k-space and an image after the Fourier transform on the entire region of the k-space, according to the present embodiment.

FIG. 5 shows an example of an image MI obtained after performance of a Fourier transform on the central region CR of the k-space KSP (hereinafter said image is referred to as a "measured image MI") and an image ZI obtained after performance of the Fourier transform on the entire region (i.e., the central region CR and the surrounding region SR combined) of the k-space (hereinafter said image is referred to as a "padding image ZI"). As shown in FIG. 5, the size of the weighted average filter WAF is set to a size DS corresponding to "3×3" pixels for the measured image MI as a default. At this time, the symbols "m" and "n" in the formulae (2) and (3) are both allocated a value of three. The size of the weighted average filter WAF, that is, a convolution filter related to an LPF may be set to 5 pixels taken in a cross shape with a pixel of interest in the center. Also, the weight of the weighted average filter WAF on a pixel of interest may be either zero or a value having an absolute value that is smaller than surrounding pixels. The black circles shown in FIG. 5 represent a plurality of pixels of the measured image MI (said pixels are referred to as "measured pixels") and a plurality of pixels of the padding image ZI respectively corresponding to the plurality of measured pixels. As shown in FIG. 5, the padding image ZI is an enlarged image of the measured image MI.

To obtain an effect similar to a result of applying the weighted average filter WAF to the measured image MI in the padding image ZI, the size DS of the weighted average filter WAF must be changed, as shown in FIG. 5. A magnification percentage of the weighted average filter corresponds to a ratio of the k-space KSP related to the first complex image CI1 with respect to the central region CR. Therefore, through the filter function 1273, the processing circuitry 127, for example, multiplies the size DS of the weighted average filter WAF by the ratio of the k-space KSP to the central region CR, to thereby determine a size CDS of the weighted average filter WAF applied to the padding image ZI. Namely, the processing circuitry 127 determines the size of the weighted average filter through the above procedures based on the information of the zero padding in the k-space. In other words, the processing circuitry 127 changes (adjusts) the size of the weighted average filter according to the magnification percentage. Next, the processing circuitry 127 applies the weighted average filter WAF having the determined size CDS to the first real-part image ReI1 and the first imaginary-part image ImI1, to thereby generate the second real-part image ReI2 and the second imaginary-part image ImI2.

(Step Sa2)

Through the denoised phase image generation function 1275, the processing circuitry 127 generates a denoised phase image DPI, from which noise has been removed by the weighted average filter WAF, based on the second real-part image ReI2 and the second imaginary-part image ImI2. The processing circuitry 127 causes the storage device 125 to store the denoised phase image DPI. In an MR image, a local change of a phase value is small (slow) with regard to the body tissue of the subject P, that is, a phase value with regard to the body tissue is uniform in the first complex image CI1. Therefore, a phase value $\theta_{lpf}(x,y)$ of the denoised phase image DPI is close to a true phase value of the first complex image CI1. In other words, the influence of the weighted average filter WAF on the phase value is limited to denoising.

Specifically, the processing circuitry 127 generates the denoised phase image DPI by calculating arc tangent ($\tan^{-1}$) for a ratio of the second imaginary-part image ImI2 to the second real-part image ReI2. More specifically, the processing circuitry 127 performs calculation of the following formula (5), to thereby generate a phase value $\theta_{lpf}(x,y)$ of a position (x,y) in the denoised phase image DPI.

$$\theta_{lpf}(x,y) = \tan^{-1}\left(\frac{b_{lpf}(x,y)}{a_{lpf}(x,y)}\right) \quad (5)$$

(Step Sa3)

Through the pseudo intensity image generation function 1277, the processing circuitry 127 generates a grayscale pseudo intensity image GSI related to an absolute value of the first complex image CI1 based on the denoised phase image DPI, the first real-part image ReI1, and the first imaginary-part image ImI1. The processing circuitry 127 causes the storage device 125 to store the pseudo intensity image GSI.

Specifically, through the pseudo intensity image generation function 1277, the processing circuitry 127 generates the pseudo intensity image GSI by adding the following products together at the same position (x,y): a product of a pixel value a(x,y) of the first real-part image ReI1 and a cosine $\cos(\theta_{lpf}(x,y))$ of the phase value $\theta_{lpf}(x,y)$ of the denoised phase image DPI; and a product of a pixel value b(x,y) of the first imaginary-part image ImI1 and a sine $\sin(\theta_{lpf}(x,y))$ of the phase value $\theta_{lpf}(x,y)$ of the denoised phase image DPI.

Figure 6:
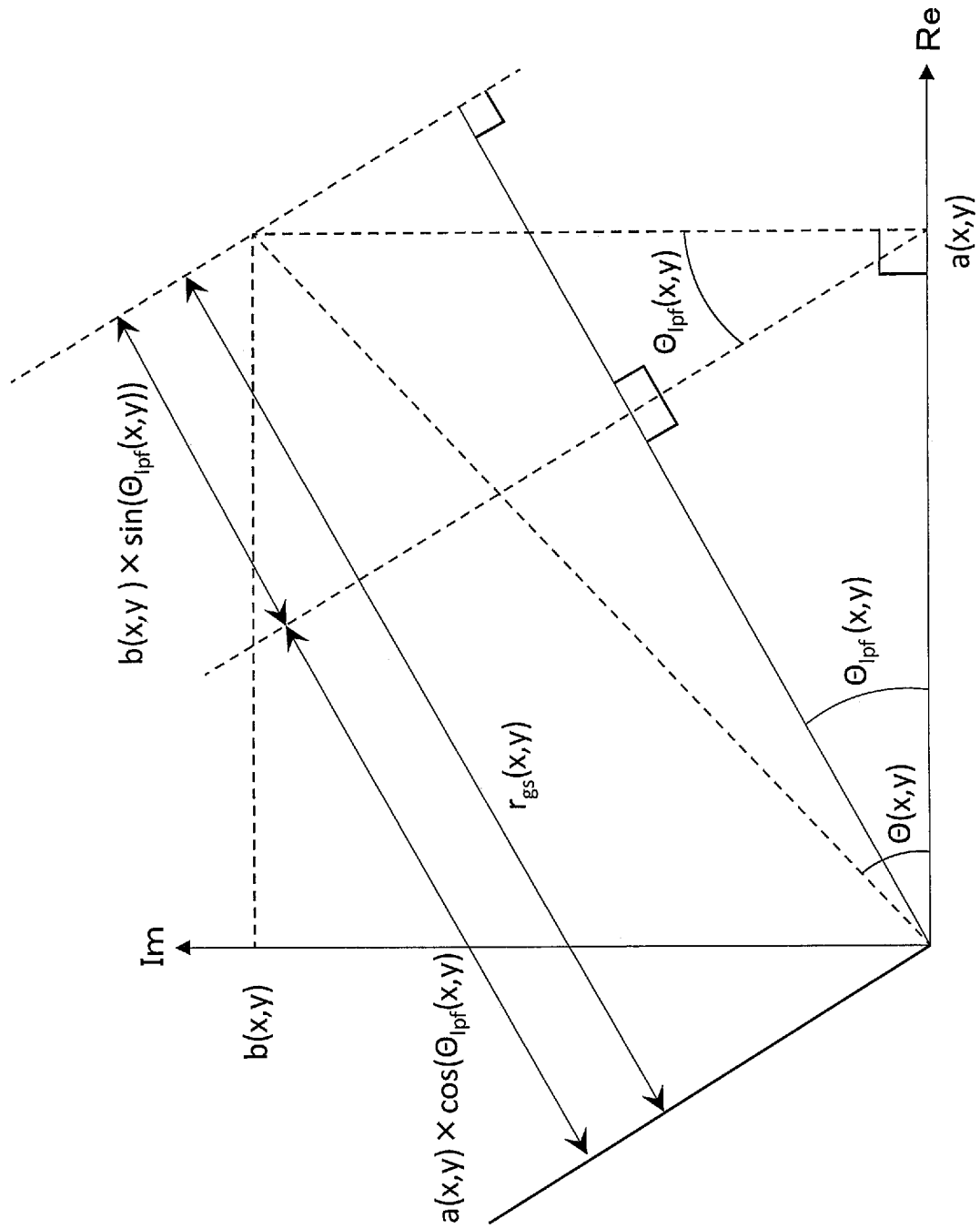
FIG. 6 is a diagram schematically showing an outline of the calculation of a pixel value rgs(x,y) of a position (x,y) in the pseudo intensity image according to the present embodiment.

FIG. 6 schematically shows an outline of calculation of a pixel value $r_{gs}(x,y)$ of the position (x,y) in the pseudo intensity image GSI. In FIG. 6, the phase value $\theta_{lpf}(x,y)$ is illustrated as being smaller than a phase value $\theta(x,y) = \tan^{-1}(b(x,y)/a(x,y))$ of the position (x,y) in the first complex image CI1, for the purpose of providing concrete descriptions. As shown in FIG. 6, the processing circuitry 127 performs calculation of the following formula (6) to thereby generate the pixel value $r_{gs}(x,y)$ of the position (x,y) in the pseudo intensity image GSI. Namely, the processing circuitry 127 generates the pseudo intensity image GSI without using the pixel value of the second complex image CI2 or the phase value $\theta(x,y)$ related to the first complex image CI1.

$$r_{gs}(x,y)=a(x,y)\times\cos(\theta_{lpf}(x,y))+b(x,y)\times\sin(\theta_{lpf}(x,y)) \qquad (6)$$

As shown in the formula (6), the pixel value $r_{gs}(x,y)$ of the pseudo intensity image GSI represents linear transformation performed on the pixel value a(x,y) of the first real-part image ReI1 and the pixel value b(x,y) of the first imaginary-part image ImI1. Namely, the calculation of the pixel value $r_{gs}(x,y)$ of the pseudo intensity image GSI does not involve a square root, as shown in the formula (6). Also, as is apparent from the formula (6), a phase value used for the calculation of the pixel value $r_{gs}(x,y)$ of the pseudo intensity image GSI is generated by the formula (5), which uses the second real-part image ReI2 and the second imaginary-part image ImI2 obtained by applying the weighted average filter WAF to each of the first real-part image ReI1 and the first imaginary-part image ImI1 independently. Therefore, the pseudo intensity image GSI is different from a general intensity image. In addition, the first real-part image ReI1 and the first imaginary-part image ImI1 are used to generate the pseudo intensity image GSI, as shown in the formula (6). Therefore, the influence of the weighted average filter WAF on the texture of the pseudo intensity image GSI is negligible. Namely, the pseudo intensity image GSI has an accurate phase value through the weighted average filter WAF, and corresponds to an intensity image that includes noise having a Gaussian distribution.

From the foregoing, the distribution of the noise of the pseudo intensity image GSI follows the same distribution form as that of the distribution of the noise of the first complex image CI1. Namely, if the noise of the first complex image CI1 follows a Gaussian distribution of a white Gaussian noise, etc., the pseudo intensity image GSI generated by the present step includes an additive noise that follows a Gaussian distribution (also referred to as a "Gaussian noise") through a linear sum of Gaussian noises, as shown in the formula (6).

(Step Sa4)

Through the denoised intensity image generation function 1279, the processing circuitry 127 generates a denoised intensity image II by performing noise reduction processing DNP on the pseudo intensity image GSI. For example, if the noise of the first complex image CI1 follows a Gaussian distribution, every local smoothing filter that is capable of removing the noise having a Gaussian distribution (e.g., a filter that adds and averages pixel values around a pixel of interest, that is, a linear sum of a plurality of pixel values included in pixels near a pixel of interest) can be applied as the noise reduction processing DNP. At this time, the average of the noise of the denoised intensity image II is close to zero.

Preferably, through the denoised intensity image generation function 1279, the processing circuitry 127 uses a trained model as the noise reduction processing DNP. The processing circuitry 127 may perform the noise reduction processing DNP on an additive pseudo intensity image to thereby generate the denoised intensity image II.

The trained model is stored in the storage device 125. Programs such as a trained model may be directly integrated into the circuitry of the processor, instead of being stored in the storage device 125. Namely, the trained model itself may be preset in an ASIC or a programmable logic device of the processing circuitry 127. In other words, the trained model may be formed using an ASIC or a programmable logic device. In this case, the processing circuitry 127 implements the denoised intensity image generation function 1279 by reading and executing the trained model incorporated into the circuitry.

The trained model is a machine learning model trained in advance using leaning data. The trained model of the present embodiment is, for example, a composite function with parameters, which is a combination of a plurality of functions. The composite function with parameters is defined by a combination of a plurality of adjustable functions and parameters. The trained model of the present embodiment may be any composite function with parameters that satisfies the above-described requirements; however, to provide concrete descriptions, the trained model of the present embodiment will be illustrated as a multi-layer network model.

The trained model using a multi-layer network model is, for example, a deep neural network (DNN), which is a multi-layer neural network targeted for deep learning. As an example of the DNN, a convolutional neural network (CNN) may be used as the trained model. The DNN includes an input layer for inputting the pseudo intensity image GSI, an output layer for outputting the denoised intensity image II, and at least one interlayer between the input layer and the output layer. It is assumed that the trained model is used as a program module which is a part of artificial intelligence software, for example.

Through the denoised intensity image generation function 1279, the trained model receives input of the pseudo intensity image GSI. Upon input of the pseudo intensity image GSI, the trained model outputs the denoised intensity image II corresponding to the noise-reduced pseudo intensity image GSI. Namely, the trained model is a multi-layer network model in which each parameter has been trained so as to output the denoised intensity image II with reduced noise upon input of the pseudo intensity image GSI. In other words, the trained model is configured to function so that it outputs the denoised intensity image II corresponding to the noise-reduced pseudo intensity image GSI based on the pseudo intensity image GSI.

Figure 7:
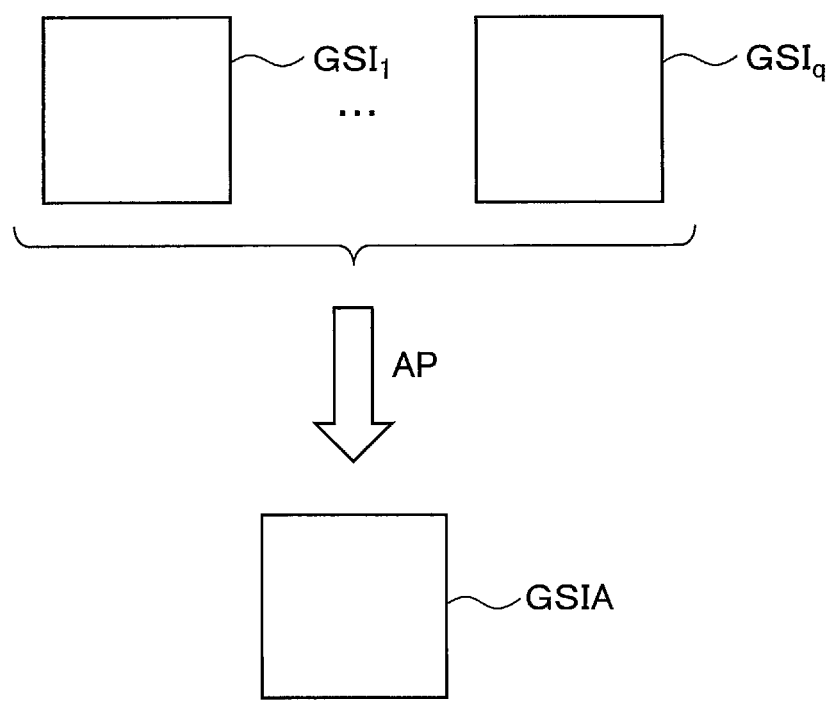
FIG. 7 is a diagram showing an example of an outline of addition processing involving the addition of a plurality of pseudo intensity images according to the present embodiment.

If a plurality of pseudo intensity images are generated by performing magnetic resonance imaging on the subject P multiple times, the processing circuitry 127 may generate, through the denoised intensity image generation function 1279, the denoised intensity image by adding the plurality of pseudo intensity images as the noise reduction processing DNP (hereinafter referred to as "adding processing"). Processing for the performance of averaging may be performed instead of the adding processing. FIG. 7 shows an example of the outline of the adding processing. As shown in FIG. 7, the processing circuitry 127 performs adding processing AP on a plurality of pseudo intensity images ($GSI_1, \ldots, GSI_q$) (q being a natural number of two or greater), to thereby generate a denoised intensity image GSIA. At this time, the S/N (signal-to-noise ratio) of the denoised intensity image GSIA improves as compared to the S/N of the respective pseudo intensity images. The processing circuitry 127 may perform various types of processing for improving S/N, such as averaging, on the plurality of pseudo intensity images, instead of adding the plurality of pseudo intensity images.

Through the system control function 1270, the processing circuitry 127 outputs the generated denoised intensity image II to the display 123 and the storage device 125. The display 123 displays the generated denoised intensity image II.

According to the configuration and the black-floating reduction process described above, the advantageous effects described below can be obtained.

According to the MRI apparatus 100 of the present embodiment, it is possible to: generate the second complex image CI2 that includes the second real-part image ReI2 and the second imaginary-part image ImI2 by applying the weighted average filter WAF to each of the first real-part image ReI1 and the first imaginary-part image ImI1 of the first complex image CI1 generated based on the magnetic resonance data MRD collected for the subject P; generate the denoised phase image DPI, from which noise has been removed by the weighted average filter WAF, based on the second real-part image ReI2 and the second imaginary-part image ImI2; and generate the pseudo intensity image GSI related to an absolute value of the first complex image CI1 based on the denoised phase image DPI, the first real-part image ReI1, and the first imaginary-part image ImI1.

Also, according to the present MRI apparatus 100, it is possible to generate the pseudo intensity image by calculating a sum of a product of a pixel value of the first real-part image and a phase value cosine of the denoised phase image and a product of a pixel value of the first imaginary-part image and a phase value sine of the denoised phase image.

According to the present MRI apparatus 100 of the present embodiment, it is possible to generate the denoised intensity image II by performing various types of noise reduction processing DNP on the pseudo intensity image GSI without estimating the noise amount.

According to the present MRI apparatus 100 of the present embodiment, it is possible to: determine the size of the weighted average filter WAF in accordance with an area ratio of the k-space to the central region CR if magnetic resonance data is arranged in the central region CR in the k-space related to the first complex image CI1 and zero is arranged in the surrounding region SR in the k-space excluding the central region CR, that is, if zero padding is performed in the k-space; and apply the weighted average filter WAF having the determined size to the first real-part image ReI1 and the first imaginary-part image ImI1.

According to the MRI apparatus 100 of the present embodiment, it is possible to generate the denoised intensity image GSIA by adding the plurality of pseudo intensity images (GSI$_1$, ..., GSI$_q$). This allows for improvement of the S/N of the denoised intensity image II according to an increase of the number of excitation (NEX), and is therefore beneficial in generating a diffusion-weighted image using a sequence of EPI as the denoised intensity image II, for example.

Therefore, according to the present MRI apparatus 100 of the present embodiment, the pseudo intensity image GSI can include noise that follows a Gaussian distribution.

From the foregoing, according to the present MRI apparatus 100, it is possible to: generate the denoised phase image DPI having a phase value $\theta_{lpf}(x,y)$ close to a true phase value of the first complex image CI1 and has a favorable S/N by using the weighted average filter WAF, which is a simple denoising means; and generate, by using the denoised phase image DPI, the first real-part image ReI1, and the first imaginary-part image ImI1, the pseudo intensity image GSI on which the noise reduction processing DNP can be easily performed, by performing linear transformation that does not cause distortion of a signal (pixel value) without adopting non-linear transformation, which is polar coordinate transformation, on the pixel values of the first real-part image ReI1 and the first imaginary-part image ImI1.

Namely, when an absolute-value image is generated by performing non-linear transformation on the first complex image CI1, a Gaussian distribution representing the noise of the first complex image CI1 is, for example, transformed into a Rayleigh distribution; however, according to the present black-floating reduction process, a distribution similar to the distribution of the noise of the first complex image CI1 is maintained in the pseudo intensity image GSI. Therefore, it is possible to: apply every smoothing filter or DNN capable of denoising the Gaussian distribution to the pseudo intensity image GSI in the noise reduction processing of the present black-floating reduction process; and reduce black floating with high precision, that is, reduce a dark and pale texture of the denoised intensity image II with high precision and display the image.

From the foregoing, according to the present MRI apparatus 100, even when magnetic resonance imaging is performed on a part of the first complex image CI1 where an area of the flat portion of the pixel value is small, it is possible to generate the denoised intensity image II with black floating as noise reduced with high precision, by applying the noise reduction processing DNP to the generated pseudo intensity image GSI. In particular, according to the present MRI apparatus 100, it is possible to further improve denoising performance for the black floating when performing magnetic resonance imaging using various high-speed sequences where S/N is small, because a bias (noise) due to the Rayleigh distribution superimposed on the intensity image is proportional to a standard deviation.

In addition, according to the present black-floating reduction process, the noise reduction processing DNP is performed not to the complex image but to the grayscale pseudo intensity image GSI; therefore, it is possible to reduce the calculation costs and improve the processing efficiency under the circumstances where high-speed MR-data collection is required.

Figure 8:
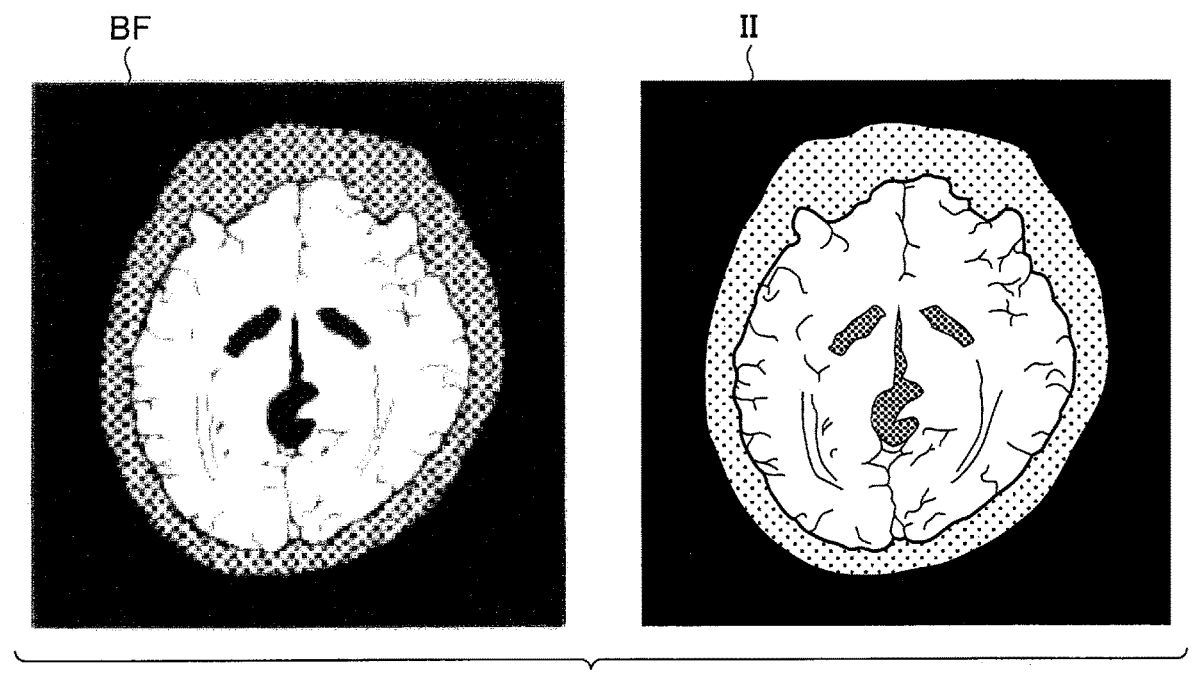
FIG. 8 is a diagram showing an example of an image that has not been subjected to the process of reducing black floating, and a denoised intensity image that has been subjected to the process of reducing black floating of the present embodiment.

FIG. 8 shows an example of the advantageous effects of the present embodiment. An image BF shown in FIG. 8 is an example of an image that has not been subjected to the black-floating reduction process of the present embodiment. An image NBF shown in FIG. 8 is an example of the denoised intensity image II that has been subjected to the black-floating reduction process of the present embodiment. As is clear from the comparison between the image BF and the denoised intensity image II, the black floating is reduced in the denoised intensity image II with high precision by the black-floating reduction process of the present embodiment.

From the foregoing, it is possible to provide an operator with the denoised intensity image II with black floating reduced with high precision by displaying the denoised intensity image II subjected to the black-floating reduction process on the display 123, and to improve the diagnostic efficiency for the subject P.

APPLIED EXAMPLE

Figure 9:
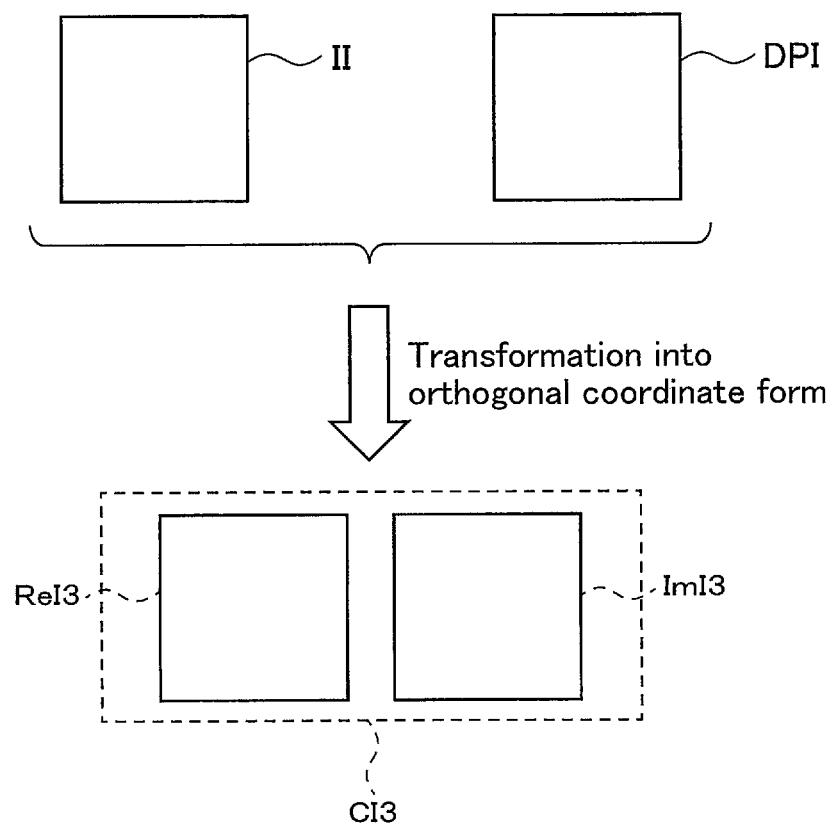
FIG. 9 is a schematic diagram showing an example of post-processing performed after the process of reducing black floating is performed, according to an applied example of the present embodiment.

An applied example will be described with regard to post-processing performed after the black-floating reduction process. FIG. 9 is a schematic diagram showing an example of the post-processing performed in the present applied example.

As shown in FIG. 9, through the complex image generation function 1271, the processing circuitry 127 generates a third complex image CI3 based on the denoised intensity image II and the denoised phase image DPI, wherein the third complex image CI3 has the pixel value of the denoised intensity image II as an absolute value of a complex number and has the pixel value of the denoised phase image DPI as an angle of deviation. Namely, the processing circuitry 127 generates the third complex image CI3 by transforming the denoised intensity image II and the denoised phase image DPI in a polar coordinate form into a third real-part image ReI3 and a third imaginary-part image ImI3 in an orthogonal coordinate form. In other words, the third complex image CI3 is generated using the denoised phase image DPI, in which noise has been reduced, and the denoised intensity image II, in which black floating has been reduced.

Specifically, through the complex image generation function 1271, the processing circuitry 127 regenerates a third complex image CI3(x,y) as a denoised complex image through the following formula (7), which uses the denoised intensity image II and the denoised phase image DPI.

$$\begin{cases} CI3(x, y) = a_{dn}(x, y) + j \times b_{dn}(x, y) \\ a_{dn}(x, y) = r_{dn}(x, y) \times \cos(\theta_{lpf}(x, y)) \\ b_{dn}(x, y) = r_{dn}(x, y) \times \sin(\theta_{lpf}(x, y)) \end{cases} \quad (7)$$

In the formula (7), $a_{dn}(x,y)$ denotes a pixel value of a position (x,y) of the third real-part image ReI3, and $b_{dn}(x,y)$ denotes a pixel value of a position (x,y) of the third imaginary-part image ImI3. Also, $r_{dn}(x,y)$ denotes a pixel value of a position (x,y) of the denoised intensity image II, and $\theta_{lpf}(x,y)$ denotes a phase value of a position (x,y) of the denoised phase image DPI.

Through an image processing function (not shown), the processing circuitry 127 performs post-processing using a complex image as a premise, through the use of the third complex image CI3 in which black floating has been reduced with high precision. The post-processing is, for example, the processing used for separating water and fat. Through the post-processing, the processing circuitry 127 generates various MR images (such as a water image and a fat image) in which black floating has been reduced with high precision (hereinafter referred to as a "black-floating-reduced MR image"). Through the system control function 1270, the processing circuitry 127 outputs the generated black-floating-reduced MR image to the display 123 and the storage device 125. The display 123 displays the black-floating-reduced MR image.

According to the configuration and the black-floating reduction process described above, the advantageous effects described below can be obtained.

According to the MRI apparatus 100 of the present applied example, the third complex image CI3 can be generated based on the denoised intensity image II and the denoised phase image DPI, wherein the third complex image CI3 has the pixel value of the denoised intensity image II as an absolute value of a complex number, and has the pixel value of the denoised phase image DPI as an angle of deviation.

Therefore, according to the MRI apparatus 100 of the present applied example, the black-floating-reduced MR image with reduced noise can be generated using the third complex image CI3 in which black floating has been reduced with high precision, and displayed on the display 123. With said feature, the MRI apparatus 100 of the present applied example can provide the black-floating-reduced MR image to the operator and improve the diagnostic efficiency for the subject P.

If the technical idea of the present MRI apparatus 100 is realized by a medical complex image processing apparatus as a modification of the present embodiment, the present applied example, etc., the medical complex image processing apparatus has, for example, the configuration in the frame 200 indicated by a dashed line in FIG. 1. At this time, the storage device 125 of the medical complex image processing apparatus 200 stores the first complex image CI1. The processing circuitry 127 reads the first complex image CI1 from the storage device 125 before performing the processing of step Sa1 of the black-floating reduction process. The processing circuitry 127 then performs the processing of steps Sa1 to Sa4. The advantageous effects of the medical complex image processing apparatus 200 are the same as those described above; therefore, the description thereof will be omitted.

Also, if the technical idea of the present MRI apparatus 100 is realized by cloud computing or the like as a modification of the present embodiment, the present applied example, etc., a server on the Internet includes, for example, the storage device 125 and the processing circuitry 127 shown in FIG. 1. At this time, the complex image generation function 1271, the filter function 1273, the denoised phase image generation function 1275, the pseudo intensity image generation function 1277, the denoised intensity image generation function 1279, etc., are realized by installing image processing programs that execute these functions in the processing circuitry 127 of the server and developing these programs on a memory. For example, the server can perform an image generation process that includes the black-floating reduction process.

Furthermore, as a modification of the present embodiment, the present applied example, etc., the technical idea related to the present MRI apparatus 100 can be realized by installing programs related to the black-floating reduction process in a computer such as a workstation, and developing these programs on a memory. The programs that allow the computer to perform said approach can also be stored and distributed in various portable storage media such as a magnetic disk, an optical disk, and a semiconductor memory.

The technical idea related to the present embodiment, the present applied example, etc., can also be applied to a medical signal that includes a complex component. For example, said technical idea can be applied to an ultrasonic diagnostic apparatus.

According to the embodiment, the applied example, etc., described above, a medical image with noise reduced can be generated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A magnetic resonance imaging apparatus comprising: processing circuitry configured to:
    apply a filter to each of a first real-part image and a first imaginary-part image of a first complex image generated based on acquired magnetic resonance data and thereby generate a second complex image that includes a second real-part image and a second imaginary-part image;

generate a phase image denoised by the filter, the denoised phase image generated based on the second real-part image and the second imaginary-part image; and generate an intensity image related to an absolute value of the first complex image based on pixel values of the denoised phase image, the first real-part image, and the first imaginary-part image.

2. The magnetic resonance imaging apparatus according to claim 1, wherein the processing circuitry is configured to generate the intensity image by calculating a sum of a product of a cosine of a phase value of the denoised phase image and a pixel value of the first real-part image and a product of a sine of the phase value and a pixel value of the first imaginary-part image.

3. The magnetic resonance imaging apparatus according to claim 1, wherein the processing circuitry is configured to generate a denoised intensity image by performing noise reduction processing on the intensity image.

4. The magnetic resonance imaging apparatus according to claim 3, wherein the processing circuitry is configured to generate a third complex image based on the denoised intensity image and the denoised phase image, the third complex image having a pixel value of the denoised intensity image as an absolute value of a complex number and having a pixel value of the denoised phase image as an angle of deviation.

5. The magnetic resonance imaging apparatus according to claim 3, wherein the processing circuitry is configured to generate the denoised intensity image by adding a plurality of the intensity images.

6. The magnetic resonance imaging apparatus according to claim 1, wherein the processing circuitry is configured to:
determine a size of the filter in accordance with an area ratio of a k-space to a central region, if the magnetic resonance data is arranged in the central region in the k-space related to the first complex image and zero is arranged in a surrounding region in the k-space excluding the central region; and apply the filter having the determined size to the first real-part image and the first imaginary-part image.

7. The magnetic resonance imaging apparatus according to claim 1, wherein the intensity image includes noise that follows a Gaussian distribution.

8. The magnetic resonance imaging apparatus according to claim 1, wherein the filter is a weighted average filter.

9. The magnetic resonance imaging apparatus according to claim 1, wherein the processing circuitry is configured to generate an intensity image related to an absolute value of the first complex image based on pixel values of the denoised phase image, the first real-part image, and the first imaginary-part image at a same position.

10. A medical complex image processing apparatus comprising:
processing circuitry configured to:
apply a filter to each of a first real-part image and a first imaginary-part image of a first complex image generated based on an acquired medical signal including a complex component and thereby generate a second complex image that includes a second real-part image and a second imaginary-part image;

generate a phase image denoised by the filter, the denoised phase image generated based on the second real-part image and the second imaginary-part image; and generate an intensity image related to an absolute value of the first complex image based on the denoised phase image, the first real-part image, and the first imaginary-part image.

* * * * *